United States Patent [19]

Bullwinkel

[11] Patent Number: 5,414,459
[45] Date of Patent: May 9, 1995

[54] FIBER OPTIC VIDEO GLASSES AND PROJECTION SYSTEM

[76] Inventor: Paul Bullwinkel, P.O. Box 1777, Jenson Beach, Fla. 34958

[21] Appl. No.: 158,626

[22] Filed: Nov. 26, 1993

[51] Int. Cl.⁶ .............................................. H04N 13/00
[52] U.S. Cl. ........................................ 348/53; 348/54; 348/359; 348/804; 128/653.2
[58] Field of Search ................. 348/804, 836, 53, 359, 348/54, 51, 77; 128/653.2

[56] References Cited

U.S. PATENT DOCUMENTS 4,310,849  1/1982  Glass ........................ 348/53
4,901,141  2/1990  Costello ................. 348/804

*Primary Examiner*—Scott A. Rogers
*Attorney, Agent, or Firm*—McHale & Slavin

[57] ABSTRACT

The instant invention is a display system that provides visual stimuli to a patient who is undergoing diagnostic treatment within a magnetic resonance imaging apparatus. The system utilizes a pair of lightweight fiber optic video glasses having a hollow chamber wherein a prism with mirrors splits a visual image supplied through a fiber optic cable connected to an LCD projector. The projector uses a series of lenses for coupling a signal received from a video interface which monitors the use of an external VCR or television utilizing a standard NTSC format video signal. The visual image is projected onto the inner surface of reflective lenses which allows the patient to view the image as well as see through the lens providing a HUD type display.

18 Claims, 2 Drawing Sheets

FIBER OPTIC VIDEO GLASSES AND PROJECTION SYSTEM

FIELD OF THE INVENTION

This invention relates generally to those products used to comfort patients undergoing diagnostic treatment and, more particularly, to fiber optic video glasses for use by patients enduring analysis within a magnetic resonance imaging apparatus.

BACKGROUND INFORMATION

The diagnostic device known as magnetic resonance imaging (MRI) has become an invaluable tool for imaging and exploring the internal body without surgery. MRI has the ability to distinguish healthy and diseased tissue, fat and muscle, and between adjacent structures within the body which other modalities cannot demonstrate. MRI utilizes safe radio waves and a magnetic field to generate the images.

In operation, a typical MRI apparatus relies upon hydrogen protons which have a dipole movement and therefore behave as would a magnetic compass. In MRI scanning, the MRI apparatus operates as a large magnet wherein the protons align with the strong magnetic field but are easily disturbed by a brief radio frequency pulse so as to alter their alignment. As the protons return to their orientation with the magnetic field, they release energy of a radio frequency. The released energy is detected and processed for display according to the signal intensity of each issue.

The magnetic coils of the MRI apparatus are permanently fixed within a large structure so as to form a large magnet with a very confining entrance known as the bore. A patient is placed upon a scanner table that is integrated with the MRI apparatus and slid into the middle of the bore. The problem with the bore is the extremely small area for placement of the patient which leads to anxiety. The large and ominous appearance of the scanner together with harsh low monotone sounds which includes both soft and loud thumping, produces an erie and unnatural experience for the patient. Any patient who exhibits claustrophobic tendencies would require sedation before entering the bore. If the patient is above average in size, the problem is exasperated.

It is well known that familiarity of surroundings reduces anxiety. The introduction of familiar images to a person placed within a confining area, such as the MRI bore, will reduce if not eliminate anxiety and certain claustrophobic tendencies of various patients. This reduction can eliminate the need for medicating the patient or the need for a restraining device, all of which may have an adverse effect on a diagnostic test. Thus, a patient who is able to listen to a family member, soft music, or watch a familiar television program will have sufficient distractions so as to avoid concentrating on the immediate surroundings which lead to increased anxiety.

A problem with introducing conventional audio or video signals into an MRI apparatus is that the device is based upon the use of radio frequency which will disrupt signal modulation. Further, the inner area of the bore produces a magnetic field which will draw metal items when magnetized. For this reason, the audio or video signal must be in a form that is not affected by the radio frequency and transmission by a mechanism that is not easily magnetized.

An attempt to address this problem is found in U.S. Pat. No. 4,901,141 which utilizes a fiber optic taper positioned within the bore of an MRI apparatus. A CRT produced image is delivered to the fiber optic taper through a coherent image guide. The fiber optic taper expands the end of the image guide so as to provide a larger viewing surface for the patient. The problem with the fiber optic taper is that it is stationary and the patient must be positioned in a fixed location so as to be able to see the end of the optic taper. Further, to prevent distortion the patient must be located directly beneath the isocenter of the taper. Thus, the disclosure does not address different size patients, patient positioning, or near and far sighted patients. For instance, a tall person may lay with their head partially outside the bore during diagnostics of the lower body whereas a child may be well encapsulated by the bore, neither of which could properly see a fixed fiber optic taper. In addition, the use of a fixed taper will interfere with auxiliary coils, such as head and c-spine coils, that require close proximity to the body. Current construction of head and c-spine coils is such that the visual field as needed for viewing a fixed positioned fiber taper is either obscured or completely blocked if the fiber taper is utilized.

Yet another known device utilized in combination with an MRI apparatus for purposes of patient comfort is a mirror optical system mounted on a spectacle frame and secured to the patient's head. In operation, the patient lies on the scanner table wearing the optical mirror system so that the patient can view over their head so as to watch a television set placed outside of the bore. The mirror mounted spectacles allow use of a head coil, c-spine, or other skin surface mounted coils. A problem with the spectacle mounted mirror system is that it blocks forward viewing and does not accommodate image tilting should the patient turn their head.

Thus, what is lacking in the art is a single device that provides the clarity of optics, the adjustability of corrective lenses, vision viewing at any location of the MRI apparatus, and the ability to provide true stereoscopic vision to the patient allowing the operator to induce visual stimuli to either eye of the patient.

SUMMARY OF THE INVENTION

The present invention satisfies this need through the provision of a pair of fiber optic video glasses used in conjunction with an imaging device that is controlled by an interface and coupled to the glasses by use of a projector and fiber optic image guide. The video glasses of the instant invention are formed from a single housing having a hollow chamber therein for placement of a movable prism that splits a visual image supplied to the glasses by the image guide. The glasses utilize reflective adjustable lenses which allows the patient to view the visual image as displayed on the inner surface of the lens as well as see through the lens.

The image to the glasses is provided through a fiber optic image guide that is coupled to a modified LCD color projector. The LCD projector converts a standard NTSC output as received from a conventional television or VCR onto a display screen. A series of lenses is used for coupling the projection display for induction into the image guide. The video interface allows the radiologic technologist to view and control the images presented to the patient.

Thus, a primary objective of the instant invention is to provide a comfortable pair of fiber optic video glasses that are worn by a patient within an MRI apparatus wherein the glasses allow the patient to view a visual image that is superimposed over the immediate surroundings.

Yet another object of the instant invention is to provide a pair of video glasses that can be worn by a patient throughout the scanner bore and the image viewed is not affected by patient head movement or the individual size of the patient.

Still another object of the instant invention is to provide a method of adjusting the visual image to the correct inter-pupillary distance of the patient.

Yet another object of the instant invention is to provide video glasses that are adjustable for use by patients who are either near or far sighted.

Another object of the instant invention is to provide video glasses that allow the technologist to control stimuli and the like visual images that reach the individual eyes of a patient with these images centered in front of each eye.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1:
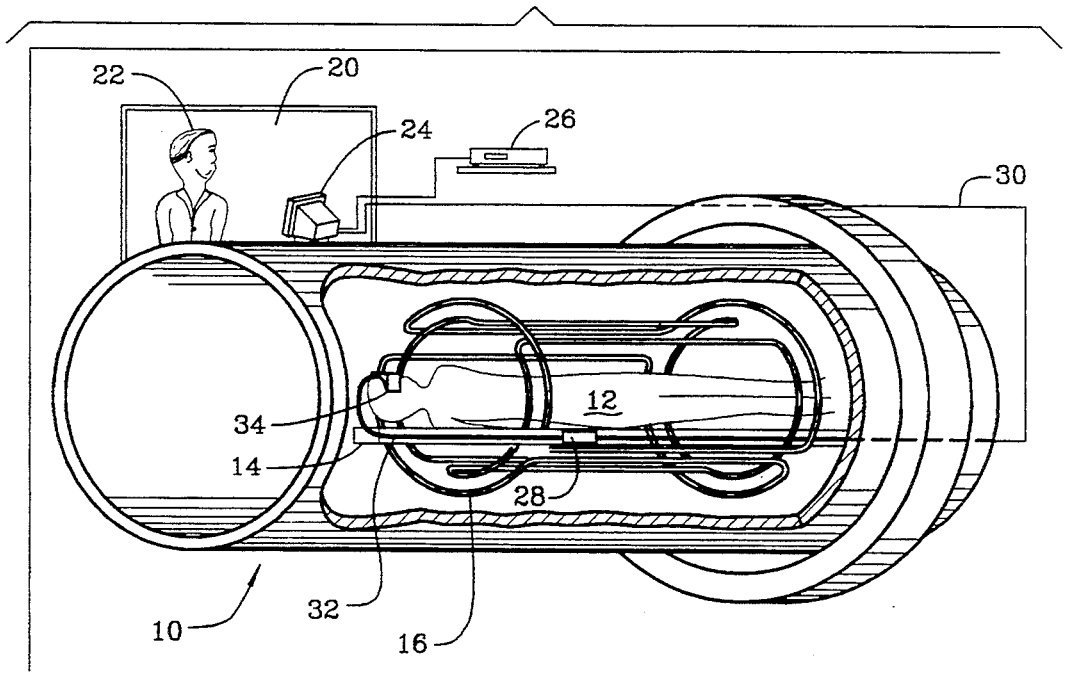
FIG. 1 is a perspective view of an MRI apparatus with the instant invention on the face of a patient lying on the MRI table.

Now referring to FIG. 1, a pictorial view of a conventional magnetic resonance image (MRI) apparatus 10 depicts a patient 12 lying on a scanner table 14 and undergoing diagnostic imaging. Imaging is performed by the use of the magnetic coils at the center of the bore to produce a magnetic gradient. The MRI apparatus 10 is placed within a shielded room 18 that is typically separated from a control room 20 to allow an operator 22 to monitor the patient 12 without disrupting the imaging process. The control room 20 and viewing glass shields both the scanning device from external interference and the operator from excess EMF's.

The display system of the instant invention controls stimuli to a patient 12 while laying in a horizontal position on the scanner table 14 by use of a video interface 24 which is coupled to a video device 26. The video device 26 can be a television, VCR, computer or the like device capable of providing a NTSC output. Location of the video device 26 can be within the scan room if distanced from the MRI apparatus 10 or otherwise shielded to prevent interfering radio frequency produced during the scan or by the video device. The closer the video device 26 is placed to the MRI apparatus, the higher the magnetic field and need for RF shielding and/or magnetic shielding properties. The video interface 24 provides a real time visual display of what the patient is viewing. In addition, the video interface 24 can be used to control the visual image delivered to the patient providing simple editing, control of the video deck, sound, and provide messages to the patient for constant communication. The video interface 24 is coupled to a projector 28 by conventional cabling 30. The projector 28 is shown mounted on the side of the scanner table 14 to reduce fiber optic length or can be mounted external the bore. An LCD color projector can be used, such as FUJIX P401 is coupled to a fiber optic image guide 32. The use of fiber optic image guides are well known in the art. The visual image is collimated to an end of the image guide by a series of lens, not shown, but include a halogen lamp with dichroic reflector through a mirror and collimator, polarizer, to the display having a 1.5×2.0 cm active area followed by a projection lens such as a 50 mm f/2.8 lens assembly and a coupling lens such as a 14.18 mm f/2.26. The second end of the image guide 32 is coupled to a pair of facially mounted fiber optic video glasses 34 available for positioning directly over each eye of the patient 12 providing visual stimuli discernable thereto. The projector provides sufficient lighting so as to compensate for attenuation of the image during transfer in the image guide.

Figure 2:
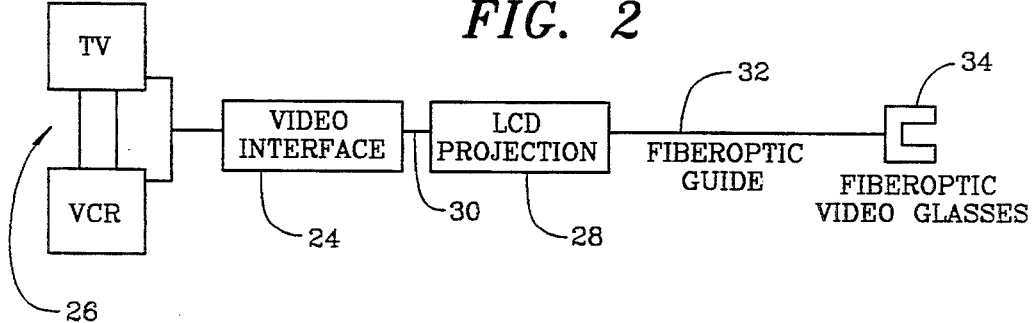
FIG. 2 is a block diagram of the visual display system.

FIG. 2 sets forth a simplified block diagram of the system wherein the video interface 24 is coupled to the video devices 26. The video interface 24 is preferably coupled to a colored liquid crystal display (LCD) projector 28 by conventional cabling 30. One end of the image guide 32 is coupled to the video glasses 34 available for positioning directly over each eye of the patient providing visual stimuli discernable thereto.

Figure 3:
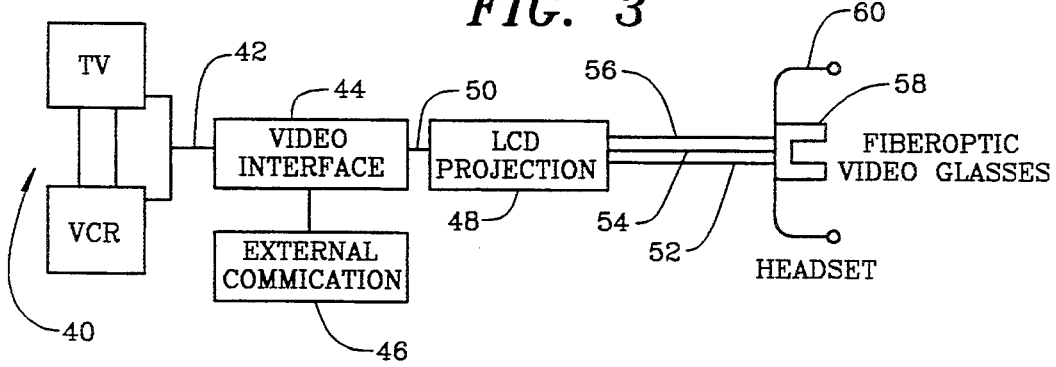
FIG. 3 is a block diagram of a second embodiment of the system having an external communicator.

FIG. 3 sets forth an alternative embodiment of the instant invention wherein the video interface 44 is coupled to at least one of the video producing devices 40. The video interface 44 is further coupled to an external communication system providing direct communication between the patient and the operation. In particular, the external communicator can attach to a video camera that allows the patient to see and communicate directly with the operator. In addition, the communication device provides a means for controlling the visual stimuli that reaches each eye of the patient. Thus, the system can be used to stimulate the patient for a specialized test, stimulate just one eye, or simply be used to alleviate anxiety. The video interface is coupled to the projector 48 by cable 50. The LCD projector 48 can be coupled to the video glasses 58 by use of a single image guide 52 as previously mentioned or true stereo vision can be obtained by use of a second image guide 54 thus eliminating the need for beam splitting disclosed later in this specification. An audio line 56 can be added so as to provide sound to accompany the visual image through the use of a headset 60 which can include a microphone channel for two-way communication. It should be noted that the detachment of the image guide from the projector allows the patient to clearly view objects outside the bore without further modification.

Figure 4:
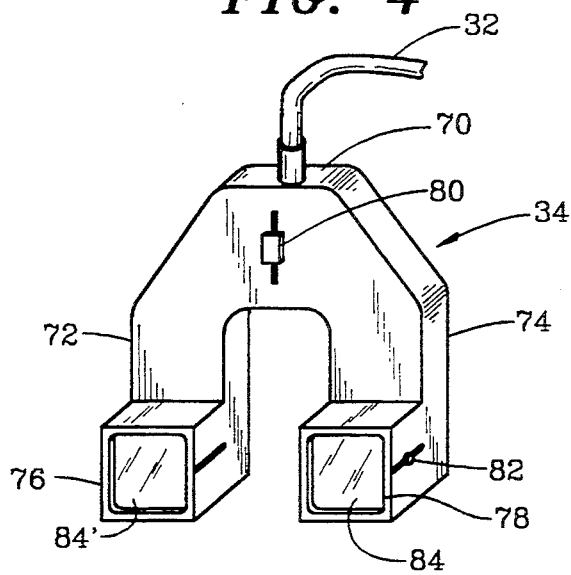
FIG. 4 is a perspective view of the facial mounted video glasses.

Now referring to FIG. 4, the facial mounted glasses 34 are illustrated with one end of the image guide 32 coupled to an input end 70 of a U-shaped hollow plastic housing forming a right chamber 72 between the input end 70 and a first display end 76 and a left chamber 74 between the input end 70 and a second display end 78. A prism is used for splitting the visual image into two separate stereoscopic images. The prism can be adjusted in a longitudinal format so as to correct for inter-pupillary distance. Similarly, a first combiner lens 84 and a second combiner lens 84' are provided for positioning over the left eye and right eye respectively. Adjustment screw 82 accommodates patients that are near sighted or far sighted.

Figure 5:
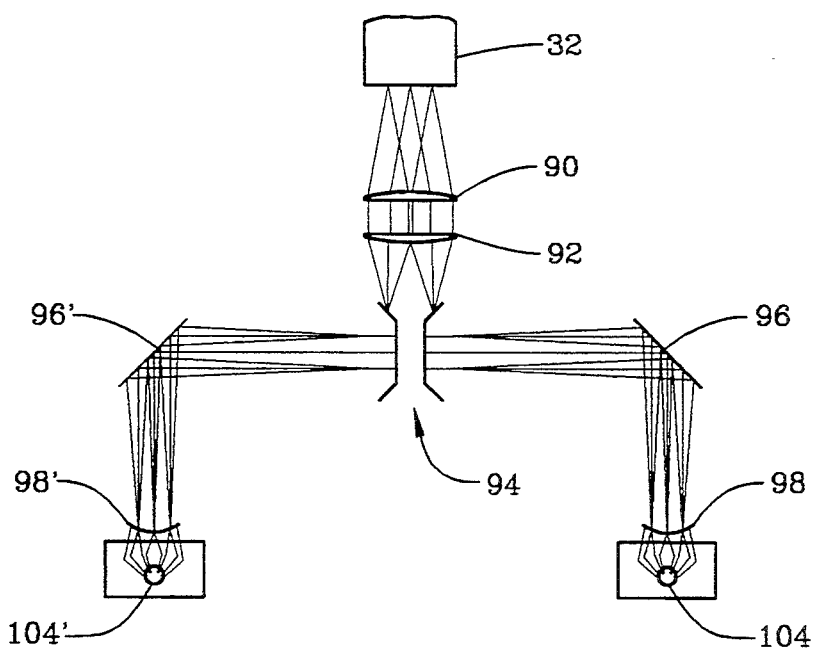
FIG. 5 is a pictorial view of the lenses placed within the video glasses.
Figure 6:
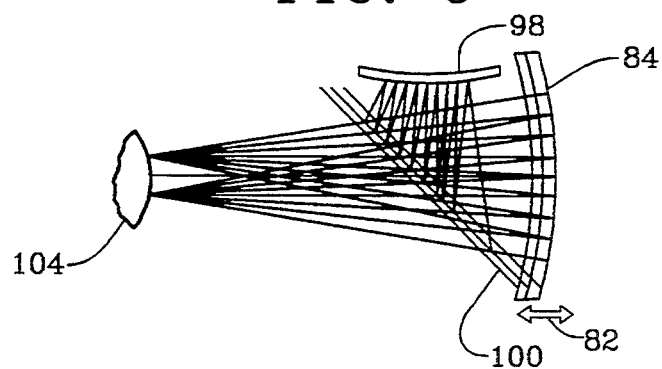
FIG. 6 is a pictorial view of the display lens positioned directly before the patient's eye.

Now referring to FIGS. 5 and 6, the inner chamber of the video glasses sets forth the arrangement of lens and mirrors for delivering the visual image to the patients' eyes. The visual image delivered from the image guide 32 is directed through relay lens 90 and 92 and onto the prism 94 used for splitting the images. The visual image is then directed to a first 96 and second 96' reflecting means for transferring the images around a 45 degree angular curve thus redirecting the visual image into a parallel plane as previously received from the image guide and relay lens.

The visual image, now placed into the parallel plane, is directed to a first 98 diffuser and second 98' diffuser/face plate for reflection and refraction on a first 100 and second 100' fold mirror to the inner surface of each respective combiner lens 84 and 84'. The fold mirror having uni-direction transparent qualities. Preferably each combiner lens has a metallic or the like coating providing a color responsive reflection. Each combiner lens 84 and fold mirror 100 is available for positioning directly over each eye 104 providing visual stimuli discernable thereto. The combination of the combiner lens 84 and fold mirror 100 permits viewing of visual stimuli as well as viewing therethrough.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A display system providing visual stimuli to a patient while lying in a horizontal position within a Magnetic Resonance Imaging (MRI) apparatus, said system comprising:

a video interface having at least one input and at least one output, said input available for coupling to at least one video device capable of providing an NTSC output;

at least one projector coupled to said output of said video interface converting said output into a visual image;

at least one flexible fiber optic image guide coupled to said projector;

means for coupling said visual image from the output of said projector into a first end of at least one said image guide; and facial mounted glasses coupled to a second end of at least one said fiber optic image guide available for positioning directly over each eye providing visual stimuli discernable thereto as transferred through said image guide, said glasses comprising:

a U-shaped hollow housing having at least one input end and a first and second display end;

means for coupling each said input end to said fiber optic image guide;

a first and second diffuser faceplates;

mirror means disposed in each said first and second display end for reflecting said visual image respectively directed through said first and second diffuser faceplates; and a first and second combiner lens having an inner surface for reflection of said visual image respectively reflected from said first and second mirror means, one said combiner lens and one corresponding said mirror means being available for positioning directly over each eye of a human providing visual stimuli discernable thereto through said first and second display end whereby said visual image is viewable.

2. The system according to claim 1 including a monitor operatively associated with said video interface displaying said visual image.

3. The system according to claim 1 including a lens on the end of said image guide.

4. The system according to claim 1 wherein said video interface includes a means for controlling said visual image.

5. The system according to claim 1 including a means for providing audio sound in combination with said visual image.

6. The system according to claim 1 wherein said glasses are coupled to two independent image guides.

7. The facial mounted glasses according to claim 1 including a means for splitting said visual images; and a first and second reflecting means for transferring said visual image into said first and second display end of said housing.

8. The system according to claim 1 wherein said combiner lens is transparent having reflective qualities.

9. A facial mounted glasses comprising:

a housing having a chamber therein providing an input end and a first and second display end, said input end available for coupling to a fiber optic image guide for receipt of visual images;

a means for splitting visual images introduced into said input end into two separate images;

a first and second reflecting means for transferring said two separate images around an angular curve respectively into said first and second display end of said housing;

a first and second diffuser means positioned so as to receive said visual images from said means for splitting respectively by said first and second reflecting means;

a first and second mirror means respectively disposed in said first and second display end for respectively transferring said visual image from said first and second diffuser means;

a first and second combiner lens having an inner surface for reflection of said visual image transferred from said first and second mirror means respectively, one said combiner lens and one corresponding said mirror means being available for positioning directly over each eye providing visual stimuli discernable thereto, each one said combiner lens and one said mirror means allowing viewing of said visual stimuli transferred onto said combiner lens.

10. The glasses according to claim 9 wherein said means for splitting is defined as a moveable prism.

11. The glasses according to claim 9 wherein said means for reflecting is defined as a plurality of mirrors disposed cooperatively within said chamber to transfer said visual image into said first and second display end of said housing.

12. The glasses according to claim 11 wherein at least one mirror reflects said visual image from said means for splitting into a parallel plane to said visual image as received from said input end.

13. The glasses according to claim 9 wherein said mirror means is further defined as a fold mirror having uni-direction transparent qualities.

14. The glasses according to claim 9 including a means for adjusting said means for splitting for accommodating inter-pupillary positioning.

15. The glasses according to claim 9 including a means for adjusting the position of said first and second combiner lens to accommodate near or far sighted patients.

16. The glasses according to claim 9 wherein each said combiner lens has a reflective coating.

17. The glasses according to claim 9 wherein said combiner lens is transparent having reflective qualities.

18. A display system providing visual stimuli to a patient while lying in a horizontal position within a Magnetic Resonance Imaging (MRI) apparatus, said system comprising:

a video interface having at least one input and at least one output, said input available for coupling to a video imaging device capable of providing a video output;

a colored liquid crystal display projector coupled to said output of said video interface converting said output into a visual image;

a flexible fiber optic image guide coupled to said projector;

means for coupling said visual image into a first end of at least one said image guide;

a facial mounted glasses having an input end coupled to a second end of at least one said image guide for receipt of said visual image, and a first and second display end;

a moveable prism for splitting said visual image into two separate images;

a first and second reflecting means for transferring said visual image into said first and second display end of said glasses;

a first and second diffuser means;

a first and second fold mirror means disposed in each said first and second display end for transferring said visual image; and a first and second combiner lens having an inner surface for reflection of said visual image, one said combiner lens and one said reflecting fold mirror available for positioning directly over each eye providing visual stimuli discernable thereto, each one said combiner lens and one said fold mirror allowing viewing of said visual stimuli transferred onto said combiner lens.

* * * * *